United States Patent [19]
Fisher et al.

[11] Patent Number: 4,795,627
[45] Date of Patent: Jan. 3, 1989

[54] TRITIUM LABELLED N-MUSTARD TYPE COMPOUNDS AND A PROCESS FOR THEIR PRODUCTION

[75] Inventors: Abraham Fisher, Holon, Israel; Israel Hanin, Pittsburgh; Donald J. Abraham, Murrysville, both of Pa.

[73] Assignee: University of Pittsburgh, Pittsburgh, Pa.

[21] Appl. No.: 662,276

[22] Filed: Oct. 18, 1984

[51] Int. Cl.$^4$ .................. A61K 43/00; C07D 203/10; C07D 203/14; C07D 203/18
[52] U.S. Cl. ................................ 424/1.1; 548/954; 548/962; 548/966; 548/968; 548/969; 548/336; 548/468; 548/546; 546/275; 564/355; 564/384; 564/389; 564/503
[58] Field of Search .................... 260/239 E; 548/954, 548/968, 969, 966; 424/1.1

[56] References Cited

PUBLICATIONS

Bourgeois et al., Chem. Abstracts, vol. 77 (1972), Entry 149331f.
Li et al., Chem. Abstracts, vol. 95 (1981), Entry 128691e.
Madelmont et al., Chem. Abstracts, vol. 99 (1983), Entry 38011m.
Mantione et al., Science, vol. 213, (Jul. 1981) p. 579.
Evans, *Tritium and its Compounds*, 2nd ed., John Wiley & Sons (1974), pp. 106–113, 127–141 and 402–405.
Fisher et al., J. Pharm. and Exp. Therap., vol. 222(1), (1982) pp. 140–145.
Madelmont et al., J. Labeled Comp. and Radiopharm., vol. 20(1), (1982), pp. 7–17.

*Primary Examiner*—Donald G. Daus
*Assistant Examiner*—William A. Teoli, Jr.
*Attorney, Agent, or Firm*—Reed Smith Shaw & McClay

[57] ABSTRACT

The present invention describes novel tritium labelled nitrogen mustard type compounds, and their aziridinium type analog, and a process for the production of same. The compounds are of value in medical research and development and also as active ingredients of pharmaceutical compositions. The compounds can be used to develop analogs of human disease states and can also be used to evaluate the mechanism of neurotransmitter regulation and function, both in vitro and in vivo.

15 Claims, No Drawings

TRITIUM LABELLED N-MUSTARD TYPE COMPOUNDS AND A PROCESS FOR THEIR PRODUCTION

ACKNOWLEDGEMENT

The invention described herein was made in part during the course of work under PHS Grant MH 34893 of the National Institute of Mental Health.

FIELD OF THE INVENTION

The present invention relates to novel tritium labelled N-mustard type compounds, and the aziridinium derivatives thereof, and to a process for their manufacture.

BACKGROUND OF THE INVENTION

A chronic deficiency in vivo in central cholinergic function, i.e., acetylcholine (ACh) as a neurotransmitter, has been implicated in a variety of neurologic and psychiatric disorders, including senile dementia of Alzheimer's type, tardive dyskinesia, Huntington's chorea, Gilles de la Tourette disease, Friedreich's ataxia, Pick's disease and Down's syndrome. Clinical data indicate that cholinergic transmission may have been compromised in persons affected with these diseases. Fisher, A. and Hanin, I., "Minireview: Choline Analogs As Potential Tools In Developing Selective Animal Models Of Central Cholinergic Hypofunction," *Life Sciences*, 27: 1615 (1980).

The cholinergic system in normal animals is unique in that it possesses certain features not attributable to other animal neurotransmitter systems. More specifically, the cholinergic system exhibits rapid hydrolysis coupled with tremendous regenerative powers. Browning, E. T., *Biology of Cholinergic Function*, eds. A. M. Goldberg and I. Hanin, pp. 187-201, Raven Press, New York (1976). In general, concentrations of choline (Ch) and acetylcholine are maintained in animals at a set level under conditions of normal function. However, in the event of a breakdown in this integrated system, a more persistent change in activity, whether a hyper- or hypoactivity, is exhibited by the cholinergic system, a hypoactivity being associated with the disorders noted above.

Acetylcholine is synthesized in nerve tissues by a reversible reaction between choline and acetyl coenzyme A:

$$Ch + AcCoA \rightleftharpoons ACh + CoA$$

This reaction is catalyzed by choline acetyltransferase (ChAT), an enzyme found both in the cytoplasmic and membrane bound form in cholinergic nerve terminals.

In order to understand the underlying mechanisms involved in the cholinergic system in the disease process, and to devise prophylactic measures to counter and possibly reverse the disease process, it is important to simulate, in animal models, whether in vivo or in vitro, the neurochemical, physiological, pharmacological and behavioral conditions inherent in the disease state. Once the deficiency in cholinergic function inherent in the disease state is reproduced in the animal model, it is feasible to explore mechanisms which will reverse, and possibly even end, the specific disease state.

In the normal animal, the cholinergic system regenerates itself efficiently and rapidly. It is, therefore, important initially to develop an agent which would selectively and persistently attenuate cholinergic activity at the nerve end terminal in vivo. A chemical agent of this type, ethylcholine aziridinium (AF64A),

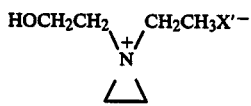

where $X'^-$ is a counter anion, has been reported and tested in rats and mice, with favorable results. The results show that AF64A is capable of inducing in selected brain areas in vivo, an irreversible inhibitory effect on the high affinity transport system for choline which is the rate limiting process for acetylcholine synthesis at the nerve terminal. Mantione, C. R., Fisher, A. and Hanin, I., "The AF64-A Treated Mouse: Possible Model For Central Cholinergic Hypofunction", *Science*, 213: 579, 1981. This irreversible inhibitory effect leads to a gradual, but eventually long-lasting cholinergic hypofunction expressed by a parallel decrease in levels of acetylcholine, and of the enzyme choline acetyltransferase in the same brain areas. Fisher, A., Mantione, C. R., Abraham, D. J. and Hanin, I., "Long Term Central Cholinergic Hypofunction Induced in Mice By Ethylcholine Aziridinium Ion (AF64A) In Vivo", *J. Pharmacol. Exptl. Ther.* 222: 140, 1982.

The effect appears to be presynaptically mediated, since postsynaptic muscarinic receptor binding was not altered by AF64A in the same preparations. Moreover, utilizing electrophysiological techniques a selective, inhibitory presynaptic localization of action of AF64A at peripheral cholinergic sites was demonstrated with cats. Mantione, C. R., DeGroat, W. C., Fisher, A., and Hanin, I., "Selective Inhibition of Peripheral Cholinergic Transmission in the Cat Produced by AF64A", *J. Pharmacol. Exptl. Ther.* 225: 616, 1983. That other neurotransmitter systems, including norepinephrine, dopamine, serotonin and gamma aminobutyric acid were unaffected by AF64A treatment further illustrates the selective cholinergic toxicity of AF64A. AF64A, thus, has a great potential as a tool for the development of an animal model of cholinergic hypofunction. Mantione, C. R., Fisher, A., and Hanin, I., "Possible Mechanisms Involved In The Presynaptic Cholinotoxicity Due To Ethylcholine Aziridinium (AF64A) In Vivo", *Life Sciences*, 35: 33, 1984.

Potent inhibition of the high affinity transport system for choline can be achieved, in vivo, by treating animals with hemicholinium-3 (HC-3). However, the effect of hemicholinium is short-lived, and is reversible. Hebb, C. O., Ling, G. M., McGeer, E. G., McGeer, P. L. and Perkins, D., "Effect Of Locally Applied Hemicholinium On The Acetylcholinic Content Of The Caudate Nucleus," *Nature*, 204: 1309, 1964. . In order to achieve a long-lasting or permanent cholinergic hypofunction one could resort to using an irreversible inhibitor of high affinity choline transport, the rate limiting step in the synthesis of acetylcholine. Only three other irreversible inhibitors of the high affinity choline transport system have been reported in the literature. These inhibitors are potential alkylating agents that can bind covalently with nucleophilic sites on the carrier. These other three reported inhibitors are the choline mustard aziridinium ion (which is the methyl analog of AF64A); the mustard analog of hexamethonium, i.e., N,N,N',N'-tetrakis-(2-chloroethyl)-1,6-hexanediamine), Fisher and Hanin, *Life Sciences,* 27: 1615, 1980, and hemicholinium 3-bromo mustard. Smart, L., "Hemicholinium 3-Bromo Mustard: A New High Affinity Inhibitor Of Sodium-Dependent High Affinity Choline Uptake," *Neuroscience,* 6: 1765 (1981). Of these three compounds, only the choline mustard aziridinium compound has also been tested by others both in vivo as well as in vitro, and its effects appear to be comparable to those of AF64A.

The utility of using AF64A both as a potential model of cholinergic disease states in vivo on the one hand and as a probe with which to inhibit the cholinergic system and to study the subsequent effects of such inhibition in vivo, on the other, is thus now known.

The availability of a radioactive labelled compound that inhibits high affinity choline transport and having high specific activity would provide an extremely useful tool in neurobiology in the understanding, diagnosis and possible countering and reversal of those disease processed involving cholinergic hypofunction or hyperfunction. The present invention relates to such novel tritium labelled N-mustard type compounds and to their aziridinium analogs, and to a method for the synthesis thereof.

SUMMARY OF THE INVENTION

The present invention relates to tritium labelled nitrogen mustard type compounds and their aziridinium analogs having the general formula:

$$R_1R_2Q$$

wherein Q is selected from the group consisting of

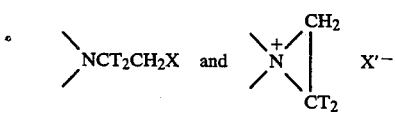

wherein $R_1$ and $R_2$ individually are hydrogen, an alkyl, a substituted alkyl, a cycloalkyl, a substituted cycloalkyl, an aryl, a substituted aryl, a heterocycloalkyl, a substituted heterocycloalkyl, a heterocycloaryl or a substituted heterocycloaryl, and $R_1$ and $R_2$ together may form a ring structure with Q of the structural formula

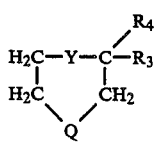

wherein

Y is —O— or —$(CH_2)_n$—, wherein n is 0 or 1, and $R_3$ and $R_4$ individually are hydrogen, hydroxyl, phenyl, naphthyl, pyrenebutyl or 4,4′-biphenylene, T is tritium, X is halogen, preferably bromine or chlorine, and $X'^-$ is a counter anion.

Preferably, $R_1$ and $R_2$ individually are hydrogen, an alkyl having up to 8 carbon atoms, a substituted alkyl having up to 8 carbon atoms, a cycloalkyl having up to 8 carbon atoms, a substituted cycloalkyl having up to 9 carbon atoms, an aryl having up to 14 carbon atoms, a substituted aryl having up to 14 carbon atoms, a heterocycloalkyl having up to 16 carbon atoms, a substituted heterocycloalkyl having up to 16 carbon atoms, a heterocycloaryl having up to 12 carbon atoms or a substituted heterocycloaryl having up to 12 carbon atoms.

The present invention further relates to a process for the production of tritium labelled nitrogen mustard type compounds having the formula

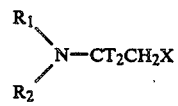

comprising reacting a compound of the formula

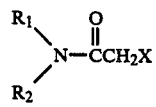

with $B_2T_6$, wherein $R_1$, $R_2$, T and X are as previously defined.

These novel tritium labelled nitrogen mustard type compounds can be used in the evaluation and development of biological models utilizing experimental animals so as to develop analogs of human disease states. The compounds can also be used to evaluate mechanisms of neurotransmitter regulation and function in vivo and in vitro and as an active ingredient in pharmaceutical compositions.

DETAILED DESCRIPTION OF THE INVENTION

The novel tritium labelled nitrogen mustard type compounds of the invention and their aziridinium analogs, have the general structural formula:

$$R_1R_2Q$$

wherein Q is selected from the group consisting of

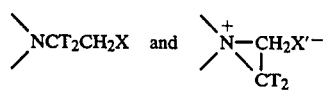

wherein $R_1$ and $R_2$ individually are hydrogen, an alkyl, a substituted alkyl, a cycloalkyl, a substituted cycloalkyl, an aryl, a substituted aryl, a heterocycloalkyl, a substituted heterocycloalkyl, a heterocycloaryl or a substituted heterocycloaryl, and $R_1$ and $R_2$ together may form a ring structure with Q of the structural formula

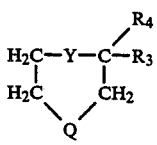

wherein

Y is —O— or —$(CH_2)_n$—, wherein n is 0 or 1, and $R_3$ and $R_4$ individually are hydrogen, hydroxyl, phenyl, naphthyl, pyrenebutyl or 4,4′-biphenylene, T is tritium, X is a halogen, preferably bromine or chlorine, and X'⁻ is a counter anion.

Preferably, $R_1$ and $R_2$ individually are a hydrogen, an alkyl having up to 8 carbon atoms, a substituted alkyl having up to 8 carbon atoms, a cycloalkyl having up to 9 carbon atoms, a substituted cycloalkyl having up to 9 carbon atoms, an aryl having up to 14 carbon atoms, a substituted aryl having up to 14 carbon atoms, a heterocycloalkyl having up to 16 carbon atoms, a substituted heterocycloalkyl having up to 16 carbon atoms, a heterocycloaryl having up to 12 carbon atoms or a substituted heterocycloaryl having up to 12 carbon atoms.

The aryl, substituted aryl, heterocycloaryl and substituted heterocycloaryl may preferably be phenyl, napthyl, pyrenyl, indole and substituted indole, morpholino and substituted morpholino, bisphenylene and substituted bisphenylene, pyrenebutyryl and substituted pyrenebutyryl. The substituted alkyls, cycloalkyls and aryls, heterocycloalkyls and heterocycloaryls may be substituted with conventional substituents, preferably such as hydroxyl, halogen, carboxy, alkylcarboxy such as β-substituted acetic acids, substituted alkylcarboxy such as β-hydroxy-β-substituted acetic acids, alkylcarboxylate such as β-substituted ethyl acetate, substituted alkylcarboxylate β-hydroxy-β-substituted ethyl acette, and mono-, di- and trialkyloxy, alkyl and aryl esters.

$R_1$ and $R_2$ jointly may also form a ring structure, preferably a cycloalkyl ring and most preferably 3-hydroxycyclopentyl, 3-hydroxycyclohexyl and 4-hydroxycyclohexyl.

Preferably, $R_1$ and $R_2$ individually are selected from the group consisting of hydrogen, methyl, ethyl, propyl, isopropyl, 2-acetoxyethyl, 2-halogenoethyl, 2-acetoxypropyl, 2-hydroxypropyl, 1-methyl-2-acetoxyethyl, γ-carboxypropyl, cyclopropyl, cyclobutyl, cyclopentyl, cyclohexyl, 2-hydroxycyclopropyl, 2-acetoxycyclopropyl, 3-hydroxycyclopentyl, 4-hydroxycyclohexyl, phenyl, napthyl, pyrenyl, 1-pyrenebutyryl, mono-, di- and trihydroxy-β-phenylethyl, mono-, di and trihydroxy-β-phenyl-αhydroxyethyl, o-methylbenzyl, o-bromobenzyl, tetrahydro-2-α-furanmethylene, 2-substituted-pyridyl, 3-substituted-pyridyl, 2-(4-imidazolyl) ethyl substituted, 5-hydroxy-3-(β-substituted ethyl) indole, γ-substituted-n-butyric acid, 2-substituted-1-(3,4-dihydroxyphenyl) ethanol, n-alkyl substituted-maleimide and tetrahydra-4-β-hydroxy-5-2-methyl-2-α-furanmethan-substituted, wherein the term "substituted", where used, designates the cite of attachment of $R_1$ or $R_2$ to Q.

$R_1$ and $R_2$ jointly preferably form a ring structure with Q of the structural formula:

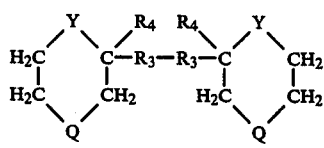

wherein
$R_3$ is a 4,4'-biphenylene moiety and $R_4$ is selected from the group consisting of hydrogen and hydroxyl.

X'⁻ is the counter anion formed in the environment in which the tritium labelled N-mustard type compound is dissolved. Preferably, it is selected from the group of counter anions consisting of hydroxide, acetate, phosphate, chloride, bromide, iodide, sulfate, carbonate and citrate.

The compounds of the invention are synthesized according to the following general reaction scheme:

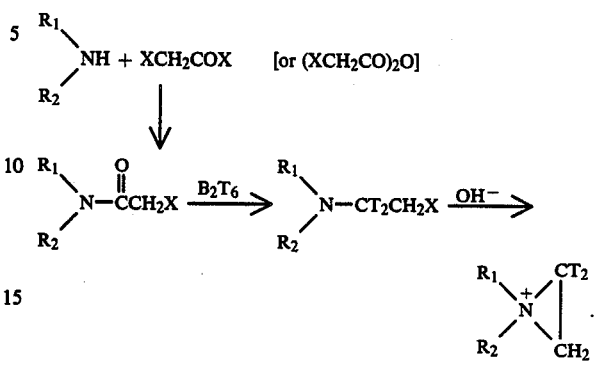

The first step of the synthesis comprises preparing the N-substituted haloacetyl derivative by reacting the respective secondary amine with haloacetyl halide or haloacetic anhydride in a suitable reaction medium such as acetonitrile or chloroform at room temperature. The next step comprises reducing the N-haloacetyl group to tritiated N-2-haloethyl using tritiated diborane in dry tetrahydrofuran, followed by addition of water and extraction into a suitable solvent, such as chloroform or ether, to give the desired product. The alternative aziridinium analog is then formed in water under basic conditions. This labelling synthesis produces compounds having a high specific radioactivity of about 10–50 Ci/mmole as determined by conventional radiochemical analyses.

The chemical process for tritium labelling the compounds of this invention is a modification of the reaction,

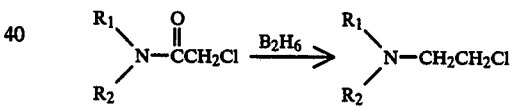

a reaction which proceeds to completion. According to the present invention, the reaction is modified to involve the tritiated analog of diborane, $B_2T_6$ (or[³H]-$B_2H_6$), which is obtained using the following single step reaction:

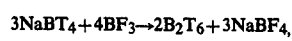

a reaction similar to that used for preparation of $B_2H_6$ (see Fieser and Fieser, *Reagents for Org. React.* 1: 199, 1967).

Ultimately, the tritiated mustard compounds can be synthesized according to the following reaction:

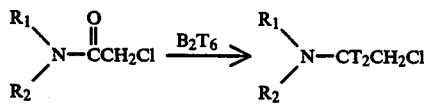

itself is obtained by reacting $R_1R_2NH$ with chloroacetic anhydride or chloroacetylchloride in a suitable solvent such as acetonitrile or chloroform. Alternatively,

can be obtained by reacting $R_1R_2NH$ with bromoacetylbromide in a suitable solvent, such as acetonitrile or chloroform. In this case $R_1R_2N-CT_2CH_2Br$ is obtained following reduction with $B_2T_6$.

The above synthesis for tritium labelled mustard compounds and their respective analogs utilizing $B_2T_6$ is novel since labelling procedures of nitrogen mustards and their aziridinium analogs have been done in the past using $T_2$ involving reduction of a carbon-carbon double bond, by general labelling if an aromatic ring was part of the molecule (e.g., Wilsheimer's Hack reaction), or by specific labelling by replacing a halogen in the molecule.

The radioactive mustards and their respective aziridinium analogs are valuable as active ingredients in pharmaceutical compositions of matter. The ethylcholine aziridinium ion (AF64A) is a highly selective presynaptic cholinotoxin. There is far less understanding of the function of central cholinergic neurons than understanding of the function of catecholaminergic or serotonergic neurons, largely due to a lack of tools with which to affect or perturb this important group of cells. An agent which is selectively toxic to the cholinergic system would be of enormous value for the investigation of the function of this system. In this regard, tritium labelled AF64A ($[^3H]$-AF64A) can be used to visualize and identify peripheral and central cholinergic pathways (e.g., utilizing histochemical and autoradiographic techniques). Moreover, since $[^3H]$-AF64A binds irreversibly to the high-affinity choline transport system, it can be used as a means to isolate and characterize biochemically those transport sites that are still an enigma since the membrane site to which choline is bound is unknown. $[^3H]$-AF64A can also be further used to investigate cholinergic processes in vitro and in vivo. One can utilize it to look at the progress of degeneration of the cholinergic system and its interaction with other neurotransmitter systems in a longitudinal dynamic manner.

Tritium labelled AF64A can also be utilized to develop more reliable animal models of disease states of central cholinergic hypofunction, e.g. senile dementia of Alzheimer's type, Pick's disease, Gestmann-Straussler syndrome, Huntington'chorea, tardive dyskinesia, childhood's schizophrenia, Gilles de la Tourette disease, Friedrich's ataxia, Down's syndrome or disease states of peripheral cholinergic hypofunction, e.g. Eaton-Lambert syndrome, Adi's disease.

Admixtures of AF64A and $[^3H]$-AF64A can be used to provide an internal marker as a radioactive cholinotoxin for central or peripheral cholinergic hypofunction and thus an adjunct to behavioral and neurochemical studies of the animal model.

$[^3H]$-AF64A can also be used to determine rates of turnover, plasticity and recovery of high affinity choline uptake sites and activity of various choline dependent enzymes in the nerve terminal (e.g., choline acetyltransferase, choline kinase and choline dehydrogenase) as well as to provide a radiolabelled marker for tissue membrane metabolism and turnover in vitro and in vivo. It will also provide a tool for studying penetration of choline-like compounds through the blood-brain barrier.

All of the above use of tritium labelled AF64A should assist in the treatment strategies of central cholinergic deficiency by providing more accurate information regarding the possible dynamics of the disease state.

The novel compounds of the may also be used as the active ingredients in pharmaceutical compositions.

EXAMPLES

The following examples are intended to illustrate the preferred embodiment of the present invention and are to be construed in a non-limiting manner.

EXAMPLE 1

Synthesis of Acetylethylcholine Mustard (Acetoxy AF64)

Step 1: Preparation of N-Chloroacetyl-N-ethylethanolamine

Chloroacetylchloride (97 g., 1 mole) in dry acetonitrile (100 ml) was added dropwise to a cold (0° C.) solution of N-ethylethanolamine (89 g., 1 mole) in acetonitrile (150 ml) and anhydrous sodium carbonate (119 g., 1.1 mole). The mixture was mechanically stirred for two hours at 0° C. and then for 14 hours at room temperature, filtered, evaporated to dryness at 40° C. and the residue was dissolved in chloroform. The resulting solution was mixed with 1N hydrochloric acid, followed by mixing with 10% aqueous sodium carbonate and aqueous saturated sodium chloride. It was then dried over anhydrous magnesium sulphate, filtered through activated charcoal and evaporated to dryness to yield N-chloroacetyl-N-ethyl-ethanolamine as a colorless oil (yield 85%) with the following indicia: MS m/e 165 (M+); 88 (M—COCH$_2$Cl); since the IR spectrum of the liquid showed two C=O peaks, one minor at λmax 1750 cm$^{-1}$ (C=O, ester) and one major at 1635 cm$^{-1}$ (C=O, amide), the compound was purified on an alumina dry column using chloroform and chloroform-:methanol (9:1) as eluents. The purified amide showed only one C=O group at 1635 cm$^{-1}$. This pure compound (pure by TLC (thin layer chromatography), NMR (nuclear magnetic resonance), IR (infrared), MS (mass spectometry) was used for the next step. The NMR (250 MHz) of the pure amide showed peaks of the two structures which are at equilibrium in such amides:

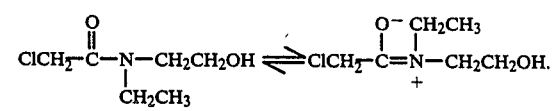

Therefore, $\delta_{CDCl_3}^{ppm}$: 4.3

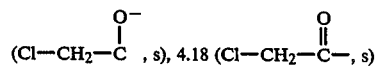

3.9-3.2 (m, —CH$_2$—N—CH$_2$CH$_2$O—); 1.18 (—CH$_3$, q, e.g., overlap of two triplets) s: singlet; m: multiplet; q: quartet.

Step 2: Preparation of N-Chloroacetyl-N-ethyl-2-acetoxyethanolamine

Route 1

Acetic anhydride (112 g, 0.11 mole) in ethylacetate (50 ml) was added dropwise to a cold (0° C.) solution of N-chloroacetyl-N-ethylethanolamine produced in Step 1 (16.5 g, 0.1 mole) in 50 ml ethylacetate. The mixture was stirred for 2 hours at 0° C., and then for 14 hours at room temperature. The organic solution was shaken with water (100 ml) and the aqueous phase extracted with chloroform. The organic phases were combined, dried over magnesium sulphate, filtered through activated charcoal and evaporated to dryness at 40° C. to produce N-chloroacetyl-N-ethyl-2-acetoxyethanolamine as a colorless oil (yield 80%). The crude compound was further purified on a dry silica column using ethylacetate as eluent. A very pure compound was obtained under these conditions (pure by TLC, NMR, IR and MS) and identified by the following indicia: MS(Cl) m/e 208 (M+); IR$\delta_{max}^{NaCl}$ cm$^{-1}$: 1740(C=O, ester), 1655(C=O, amide). The NMR (250 MHz) of the pure product showed peaks of the two structures which are at equilibrium in such amides:

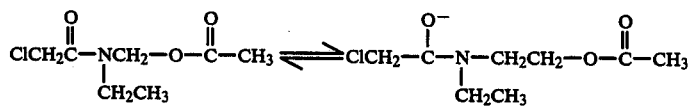

Therefore, $\delta_{CDCl_3}^{ppm}$: 4.25

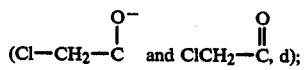

4.18 (t, CH$_2$—O—); 3.75–3.1 (m, CH$_2$—N—CH$_2$); 2.05 (d, CO—CH$_3$); 1.18 (—CH$_3$, q, e.g. overlap of two triplets). m=multiplet, t=triplet, q=quarter, d=doublet.

Route 2

N-chloroacetyl-N-ethyl-2-acetoxyethanoline can also be prepared using the following synthesis:

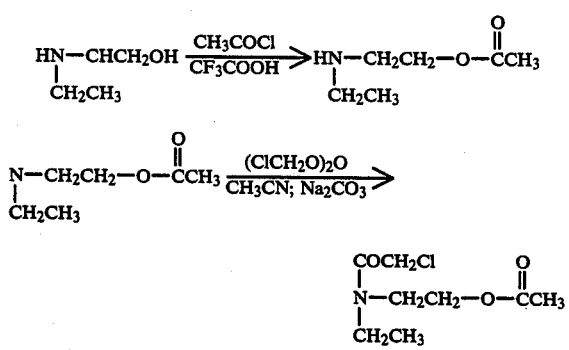

N-ethylethanolamine (52.7 g, 0.59 mole) was cooled to 0° C. and cold trifluoroacetic acid (100 ml) was added dropwise. The solution was magnetically stirred and acetylchloride (46.3 g, 0.59 mole) was added dropwise to the cold solution (0° C.). The mixture was stirred at 0° C. for 2 hours, then for 14 hours at room temperature. The mixture was evaporated to dryness at 40° C. and the residue was dissolved in chloroform. The organic solution was shaken with 10% aqueous sodium carbonate and aqueous saturated sodium chloride, dried over anhydrous magnesium sulphate, filtered through activated charcoal, and then evaporated to dryness to produce N-ethyl-2-acetoxyethanolamine as a colorless oil (yield 80%) with the following indicia:

MS: m/e130 (M+); IR$\lambda_{max}^{NaCl}$ 1735 cm$^{-1}$.

The corresponding hydrochloride salt can be precipitated by dissolving the oil in ether and acetone and adding etheral gaseous hydrochloric acid.

Chloroacetic anhydride (4.52 g, 0.026 mole) in dry acetonitrile (25 ml) was next added dropwise to a solution of N-ethyl-2-acetoxyethanolamine (2.6 g, 0.02 mole). The mixture was stirred at room temperature for 20 hours, filtered and evaporated to dryness at 40° C. The same work-up procedure as described for the Route 1 synthesis produced N-chloroacetyl-N-ethyl-2-acetoxyethanolamine (yield 90%) having the same structure and purity as the compound prepared by Route 1 (as checked by TLC, IR, NMR and MS).

Step 3: Preparation of Acetylethylcholine Mustard (Acetoxy AF64)

A solution of N-chloroacetyl-N-ethyl-2-acetoxyethanolamine (0.2 g., 1 mmol) was dissolved in 5 ml dry tetrahydrofuran (THF) which had been distilled on lithium aluminum hydride and kept on Na under a gentle stream of dry N$_2$ in a 50 ml reaction flask. The reaction flask was cooled to 0° C. and diborane (IM), B$_2$H$_6$ (obtained from Aldrich), in THF (10 ml, 10 mmol) was slowly added with a syringe (equipped with a hypodermic needle) through a rubber septum to the magnetically stirred solution of N-chloroacetyl-N-ethyl-2-acetoxyethanolamine in THF kept under a positive N$_2$ pressure.

The solution was stirred at 0°–5° C. for 4 hours and then kept for five days under a positive pressure of N$_2$ at room temperature (20°–25° C.). After five days excess diborane was destroyed by a dropwise addition of H$_2$O (10 ml) with a syringe through the rubber septum. Then NaHCO$_3$ (solid; ≈0.5–1 g.) was added until the solution pH was 7.8–8 (as checked with universal pH paper). The reaction solution was next immediately extracted with chloroform (3×5 ml). The chloroformic layer was separated in a separatory funnel and washed once with 5 ml of saturated NaCl solution in water, dried with anhydrous MgSO$_4$, and evaporated at 40°–50° C. to dryness. The TLC analysis of the reactants and reaction products if given below in Table 1.

TABLE 1

Description of TLC analysis (results, conditions, reagents) of the Starting Material, Pure Acetoxy-AF64 and the Product of Reduction

| TLC plate | Eluant | Rf of Starting Material (I) | Rf of Pure Acetoxy AF64 | Rf of Product of Reduction |
|---|---|---|---|---|
| Silica Gel (Merck #5567) | Ethyl Acetate: Hexane (1:1) | 0.4 | 0.6 | 0.6<br>0.1 (impurity) |
| Silica Gel (Riedel de Haen #37341) | Ethyl Acetate: Hexane (1:1) | 0.4 | 0.8 | 0.8<br>0.2 (impurity) |
| Aluminum Oxide (Merck #5581) | Ethyl Acetate: Hexane (9:1) | 0.5 | 0.7 | 0.7<br>0.2 (impurity) |

The reagents used for visualization on the TLC plates were iodine vapors, 4(p-nitrobenzyl)pyridine (NBP) in acetone, and ethyl bis(2,4-dinitrophenyl acetate) (EDA). The iodine vapors give an indication of all the peaks. NBP detects alkylating agents. The NBP is first dissolved in acetone (1% weight/volume). The TLC plate is quickly immersed into this solution and then withdrawn from it. Alternatively, this solution may be sprayed onto the TLC plate. Then the plate is heated on a hot plate or with a very hot stream of air, such as from a hair-dryer, until faint blue spots appear on the TLC plate. At this point the hot TLC plate is immersed into a 2% solution of NaOH in ethanol or a saturated solution in EtOH. Alternatively, this solution may be sprayed on the plate. Alkylating compounds will appear as blue spots against a white-yellowish background when the plate is dry. EDA (0.1% in acetone, methanol free) is a sensitive reagent specifically developed for visualizing amines, especially tertiary amines. The TLC plate is immersed into this solution and then quickly withdrawn. Amines appear as blue spots against a white background when the plate is dry.

The use of these three visualizing reagents and the $R_f$ of the respective peaks give an accurate picture of the reaction mixture. Thus, the iodine will color all the peaks in the reaction mixture; the NBP reagent will color all the alkylating agents, including the N-chloroacetyl-N-ethyl-2-acetoxyethanolamine; and the EDA reagent will color only the amines, thus excluding the starting compound, which is an amide.

At this point, the expected product, (Acetoxy AF64), can be purified by preparative TLC (alumina or silica gel), or by a very short dry column of alumina or silica. Alternatively, the product can also be used purified by the following technique: add dry THF (3 ml) to the residue (oil) left after evaporating the CHCl3, and cool the solution formed to 0° C. Then add etheral (gaseous HCl) dropwise (ca. 0.5 ml) until the pH becomes acidic (universal pH paper). The solution is then cooled (0°-5° C.) for 2 hours and an oil is observed on the walls of the flask. The presence of oil on the flask walls is accentuated by a further addition of dry ether (ca. 0.3 ml). The clear solution was decanted and saved, and the oil on the walls of the flask was carefully washed twice with dry ether (3 ml each time). The oil on the walls of the flask was determined to be the compound Acetoxy AF64.HCl, and other impurities (less than found in the crude original product). The oily Acetoxy AF64.HCl and impurities are stable (−20° C.) for at least a few days.

Purification of Acetoxy AF64.HCl

To the oily Acetoxy AF64.HCl with impurities is added 2 ml of H2O with NaHCO3 (pH should be 8) and which is then extracted with CHCl3 (3×5 ml), dried over MgSO4, and filtered and evaporated to dryness. The TLC gave almost the same pattern as shown earlier, although it would appear that the product, Acetoxy AF64 (free base) was purer than before.

A further purification can be achieved by preparative TLC, for instance using Merck #5717 PLC plates of silica gel 60F, and by using ethyl acetate:hexane, 1:1 as an eluent. The band corresponding to Acetoxy AF64 was scraped-off, crushed to a uniform powder, and transferred to a glass column with CHCl3:methanol (8:2). Evaporation of the solvent yielded pure Acetoxy AF64.

EXAMPLE 2

Synthesis of [$^3$H]-Acetoxy AF64

The method used to synthesize Acetoxy AF64 described in Example 1 was applied using tritium diborane, $B_2T_6$, to synthesize [$^3$H]-Acetoxy AF64, tritium labelled Acetoxy AF64. The resulting radioactive compound as synthesized having a specific radioactivity of 29 Ci/mmole was obtained ultimately as a free base in absolute ethanol at a concentration of 1 ci/ml. The compound kept under $N_2$ is stable at −20° C. for at least five months.

EXAMPLE 3

Synthesis of [$^3$H]-AF64A

[$^3$H]-AF64A can be prepared as shown in the reaction sequence presented below by diluting the solution of [$^3$H]-Acetoxy AF64 prepared in Example 2 in ethanol with water to the desired concentration and adding 10N NaOH to bring the pH of the solution to 11.3-11.7. The pH is maintained while stirring for 30 minutes at room temperature. Then the pH is lowered to 7.0 with concentrated HCl and adjusted to 7.4 with solid NaHCO3 or phosphate buffer (pH 7.4). This solution is stable at 0°-4° C. for at least 8 hours.

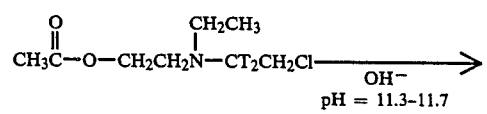

-continued

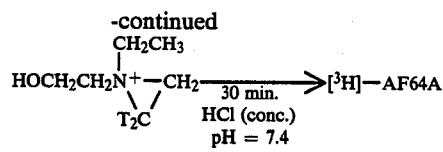

EXAMPLE 4

Synthesis of [³H]-Acetoxy AF64A

[³H]-Acetoxy AF64A is prepared by diluting a solution of [³H]-Acetoxy AF64 prepared in Example 2 in ethanol with phosphate buffer (pH 7.4) to the desired concentration as shown in the reaction sequence presented below. The conversion to the aziridinium structure is maximum (80–95%) after one hour at room temperature. This compound is stable for at least 8 hours at 0°–4° C.

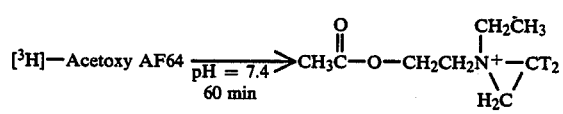

EXAMPLE 5

Synthesis of N-Chloroacetyl-N-ethyl-2-chloroacetoxyethanolamine

N-chloroacetyl-N-ethyl-2-chloroacetoxyethanolamine was prepared in one step from N-ethylethanolamine (8.9 g., 0.1 mole) and chloroacetylchloride (97 g., 1 mole) in dry acetonitrile (100 ml) and anhydrous sodium carbonate (1.19 g., 0.11 mole) by mixing at room temperature for 48 hours. The resulting product was produced in an 80% yield following the same work-up procedure as described for N-chloroacetyl-N-ethylethanolamine in Example 1. The product shows the same behavior in the NMR spectrum in COCl₃ as in N-chloroacetyl-N-ethyl-2acetoxyethanolamine due to the following equilibrium:

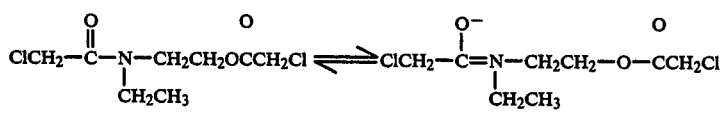

Therefore, $\delta_{CDCl_3}^{ppm}$: 4.35 (t, CH₂—O); 4.17, 4.125

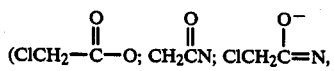

two overlapping doublets); 3.8–3.25 (m, CH₂—N—CH₂); 1.23 (q, —CH₃, e.g., two overlapping triplets). m=multiplet, q=quarter, t=triplet The reduction method using $B_2H_6$ to synthesize chloroacetyl.AF64 and using [³H]-$B_2H_6$ to synthesize [³H] chloroacetyl AF64 is similar to that described for the synthesis of Acetoxy.AF64 (or [³H]-Acetoxy.AF) in Examples 1 and 2, respectively.

Other tritium labelled nitrogen mustard type compounds and their aziridinium type analogs, in accordance with the invention compounds, can be prepared by analogous synthesis routes.

The compounds of the present invention can be formulated into pharmaceutical compositions of matter or vehicles by conventional means known to those in the art using conventional diluent adjuvants and the like.

The compounds can be administered into laboratory animals, such as rodents, rabbits, cats, dogs, and monkeys, by peripheral or intracerebral injections, by infusion or per os. However, the dosage and the route of administration need to be adjusted according to the specific biological use of the tritium labelled compounds of the invention. Table 2 presented below indicates some of the potential uses of [³H]-AF64A:

TABLE 2

| | | Striatum | |
|---|---|---|---|
| | Experimental Conditions | Effect | Result |
| Synaptosomes | A [+Na⁺] vs. [+Na⁺+Ch] | Accumulation | 10–22 fmol/μg protein |
| | B [−Na⁺] vs. [−Na⁺+Ch] | Slight Accumulation | 1–4 fmol/μg protein |
| | C [+Na⁺] vs. [−Na⁺] | Accumulation | 1–10 fmol/μg protein |
| Membranes | A [Na⁺] vs. [Na⁺+Ch] | Slight Accumulation | 1–2 fmol/μg protein |
| | B [−Na⁺] vs. [−Na⁺+Ch] | Accumulation | 1–10 fmol/μg protein |
| | C [+Na⁺] vs. [−Na⁺] | Largest Accumulation | 20–40 fmol/μg protein |

As shown in Table 2 at striatal synaptosomes or membranes (lysed synaptosomes) were incubated for 10 minutes at 30° C. in the presence of [³H]-AF64A (0.1–3 μM) in Tris buffer at pH 7.5. Tissue samples were collected onto 6F/F filters by gentle vacuum filtration. "Accumulation" represents the accumulated radioactivity into the various samples tested. The conditions A and C represent Na+—dependent high affinity [³H]-AF64A transport into the rat striatal synaptosomes. Condition B represents Na—independent transport of [³H]-AF64A into the rat striatal synaptosomes. In the case of the rat striatal membranes there is no more transport into the synaptosomes and the accumulation represents only binding to the membrane, with the largest accumulation with membranes being under condition C.

From Table 2 it is evident that [³H]-AF64A is taken up into the synaptosomes via a high affinity [Na] dependent transport system that is most probably the same system that is the choline carrier. In case of the lysed synaposomes ("membranes") [³H]-AF64A binds strongly to this carrier without involving the uptake process itself. [³H]-AF64A can, thus, be used to study binding to this carrier as well as to study uptake processes in synaptosomes obtained from different areas of the brain of experimental animals.

Although the invention has been described in detail in the foregoing for the purposes of illustration, it is to be understood that such detail is solely for that purpose and that variations can be made therein by those skilled in the art without departing from the spirit and scope of the invention except as it may be limited by the claims.

What is claimed is:

1. A tritium labeled nitrogen mustard type compound of the structural formula:

$R_1R_2Q$ wherein Q is

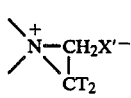

wherein $R_1$ and $R_2$ individually are from the group consisting of hydrogen, methyl, ethyl, propyl, isopropyl, 2-acetoxyethyl, 2-halogenoethyl, 2-acetoxypropyl, hydroxyethyl, 2-hydroxypropyl, 1-methyl-2-acetoxyethyl, γ-carboxypropyl, cyclopropyl, cyclobutyl, cyclopentyl, cyclohexyl, 2-hydroxycyclopropyl, 2-acetoxycyclopropyl, 3-hydroxycyclopentyl, 4-hydroxycyclohexyl, phenyl, napthyl, pyrenyl, 1-pyrenebutyryl, mono-, di and trihydroxy-β-phenyl-α-hydroxyethyl, o-methylbenzyl, o-bromobenzyl, γ-substituted-n-butyric acid, and 2-substituted-1-(3,4-dihydroxyphenyl)ethanol, wherein the term "substituted", where used, designates the cite of attachment of $R_1$ or $R_2$ to Q wherein T is tritium
X is halogen, and
$X'-$ is an anion.

2. The compound of claim 1 wherein X is a halogen selected from the group consisting of chlorine and bromine.

3. The compound of claim 1 wherein $R_1$ is —CH$_2$CH$_3$, $R_2$ is —CH$_2$CH$_2$OH, Q is

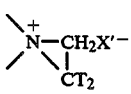

and $X'-$ is Cl$^-$.

4. The compound of claim 1 wherein $R_1$ is —CH$_2$CH$_3$, $R_2$ is —CH$_2$CH$_2$OCOCH$_3$, Q is

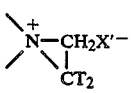

and $X'-$ is Cl$^-$.

5. The compound of claim 1 wherein $R_1$ is —CH$_3$, $R_2$ is —CH$_2$CH$_2$OH, Q is

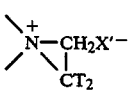

and $X'-$ is Cl$^-$.

6. The compound of claim 1 wherein $R_1$ is CH$_3$, $R_2$ is —CH$_2$CH$_2$OCOCH$_3$, Q is

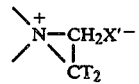

and $X'-$ is Cl$^-$.

7. The compound of claim 1 wherein $R_1$ is —CH$_2$CH$_2$CH$_3$, $R_2$ is —CH$_2$CH$_2$OH, Q is

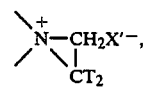

and $X'-$ is Cl$^-$.

8. The compound of claim 1 wherein $R_1$ is cyclopropyl, $R_2$ is —CH$_2$CH$_2$OH, Q is

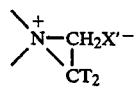

and $X'-$ is Cl$^-$.

9. The compound of claim 1 wherein $R_1$ is —CH$_2$CH$_3$, $R_2$ is 2-hydroxycyclopropyl, Q is

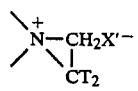

and $X'-$ is Cl$^-$.

10. The compound of claim 1 wherein $R_2$ is selected from the group consisting of H, —CH$_3$ and —CH$_2$CH$_3$ and $R_1$ is

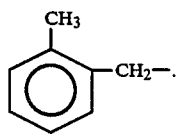

11. The compound of claim 1 wherein $R_2$ is selected from the group consisting of H, —CH$_3$, —CH$_2$CH$_3$ and $R_1$ is

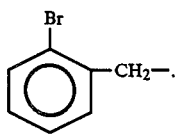

12. The compound of claim 1 wherein $R_2$ is selected from the group consisting of H, —CH$_3$, —CH$_2$CH$_3$ and $R_1$ is

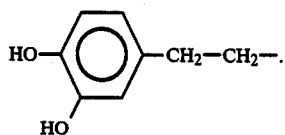

13. The compound of claim 1 wherein $R_2$ is selected from the group consisting of H, —$CH_3$, —$CH_2CH_3$ and $R_1$ is HOOC—$CH_2CH_2CH_2$—.

14. The compound of claim 1 wherein $R_2$ is selected from the group consisting of H, —$CH_3$, —$CH_2CH_3$ and $R_1$ is

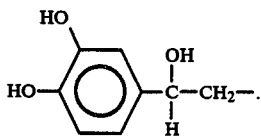

15. A pharmaceutical composition used to evaluate the mechanism of neurotransmitter hypofunction and hyperfunction comprising an effective amount of the compound of claim 1 as an active ingredient.

* * * * *

UNITED STATES PATENT AND TRADEMARK OFFICE
CERTIFICATE OF CORRECTION

PATENT NO. : 4,795,627

DATED : January 3, 1989

INVENTOR(S) : Abraham Fisher, Israel Hanin, Donald J. Abraham

It is certified that error appears in the above—identified patent and that said Letters Patent is hereby corrected as shown below:

Column 3, line 19, the word "processed" should read -- processes -- .

Column 3, line 63, the term "8 carbon atoms" should read -- 9 carbon atoms -- .

Column 5, lines 24-25, the term "substituted alkylcarboxylate β-hydroxy- β-substituted ethyl acette" should read -- substituted alkylcarboxylate β-hydroxy- β-substituted ethyl acetate -- .

Column 5, line 40, the term "trihydroxy- β-phenyl- αhydroxyethyl" should read -- trihydroxy- β-phenyl- α-hydroxyethyl -- .

Column 8, line 60, the term " $\delta CDCl_3 ppm$ " should read -- $\int_{CDCl_3} ppm$ -- .

Column 9, line 21, the phrase "208(M$^+$);IR max$^{NaCl}$cm-1" should read

-- 208(M$^+$+1 ;IR $\int_{max}^{NaCl}$ cm-1 -- .

UNITED STATES PATENT AND TRADEMARK OFFICE
CERTIFICATE OF CORRECTION

PATENT NO. : 4,795,627

DATED : January 3, 1989

INVENTOR(S) : Abraham Fisher, Israel Hanin, Donald J. Abraham

It is certified that error appears in the above—identified patent and that said Letters Patent is hereby corrected as shown below:

Column 9, line 37, the phrase " $\delta CDCl_3^{ppm}$ " should read

-- $\int_{CDCl_3}^{ppm}$ -- .

Column 13, line 63, the phrase " $\delta CDCl_3^{ppm}$ " should read

-- $\int_{CDCl_3}^{ppm}$ -- .

Signed and Sealed this

Nineteenth Day of September, 1989

Attest:

DONALD J. QUIGG

Attesting Officer        Commissioner of Patents and Trademarks